(12) United States Patent
Tripathi et al.

(10) Patent No.: US 6,692,945 B2
(45) Date of Patent: Feb. 17, 2004

(54) PROCESS FOR THE PRODUCTION OF POLYHYDROXYOCTANOATE BY STREPTOMYCES LIVIDANS

(75) Inventors: Gyanendra Tripathi, Maharashtra (IN); Lata Hanamantrao Mahishi, Maharashtra (IN); Turaga Venkata Naga Ramachander, Maharashtra (IN); Shuban Kishen Rawal, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 73 days.

(21) Appl. No.: 09/754,112

(22) Filed: Jan. 5, 2001

(65) Prior Publication Data

US 2002/0090687 A1 Jul. 11, 2002

(51) Int. Cl.$^7$ .................................................. C12P 7/62
(52) U.S. Cl. ................. 435/135; 435/252.3; 435/252.8; 435/253.5; 435/320.1; 436/23.1
(58) Field of Search .............................. 435/135, 252.3, 435/252.8, 253.5, 320.1; 536/23.1

(56) References Cited

U.S. PATENT DOCUMENTS 4,921,801 A * 5/1990 Rao et al. ................ 435/172.3

OTHER PUBLICATIONS

"Transformation and Transfection in Streptomyces"; and "Transformation of Streptomyces Protoplasts wi Plasmid DNA" from Transformation and Transpection by The John Innes Foundation, Norwic England, pp. 104–107.
"Poly Hydroxy Kanoic Acids—A Steinbuechel" from Biomaterials Ed. David Byrom, Macmillan Publishers Ltd., 1991, pp. 125–127.
"Construction of *Escherichia coli*–Streptomyces shuttle vectors transducible in Streptomyces" Authors: Morino, Tomio et al.—One sheet (Abstract).
"Construction of *Escherichia coli*–Streptomyces shuttle vectors for gene expression in Streptomyces" Authors: Yang, Runnying et al.—One sheet (Abstract).
Synthesis and production of poly(3–hydroxyvaleric acid) homopolyester by Chromobacterium violaceum Authors: Steinbuechel, Alexander.—One sheet (Abstract).
"Formation of Poly–β–hydroxybutyrate by Actinomycetes" by L.V. Kannan and Z Rehacek, indian Journal Biochemistry, vol. 7, Jun. 1970, pp. 16–129.
Micro Review—Physiology and molecular genetics of poly(β–hydroxy–alkanoic acid) synthesis in *Alacaligenes eutrophus* by A. Steinbuchel and H.G. Schlegel; Molecular Microbiology (1991) 5 (3), pp. 535–542.

"Multifunctional *Escherichia coli*—Streptomyces shuttle vectors allowing white screening on Xgal plates", by F. Wehmeier, U.F., Gene, 165 (1995) 149–150.
"A general method for identification of polyhydroxyalkanoic acid synthase genes from pseudomonads belonging to the rRNA homology group 1" by Arnulf Timm et al., Applied Microbiology and Biotechnology (1994) 40, pp. 669–675.
"Formation of Polyesters by *Pseudomonas oleovorans*: Effect of Substrates on Hydroxyalkenoates" by Roland G. Lageveen et al., Applied and Environmental Microbiology, vol. 54, No. 12, Dec. 1988, pp. 2924–2932.
"Recent Advances in and Prospects of Antibiotic Research" by J. Berdy, Ph.D., Process Biochemistry, Oct./Nov. 1980, pp. 28–35.
Nuclear Magnetic resonance Studies on Unusual Bacterial Copolyesters of 3–Hydroxybutyrate and 4–Hydroxybutyrate by Doi, Y. Kunioka, M. Nakamura, Y. and Soga, K., macromolecules, 21, (1988), pp. 2722–2727.
"Transfer of Plasmid pTO1 from *Escherichia coli* to various representatives of the order Actinomycetales by intergeneric conjugation", by Voeykova, T., Emelyanova, L., Tabokov, V. and Mkrtumyan, N., FEMS MicroBiol. Letters, 162 (1998), pp. 47–52.
"Cosmid Shuttle Vectors for Cloning and Analysis of Streptomyces DNA" by R. Nagaraja Rao et al., Methods in Enzymology, vol. 153, pp. 166, 167, 178–181.
"Construction of a new cloning vector utilizing a cryptic plasmid and the highly expressed melanin–synthesizing gene operon from *Streptomyces castaneoglobisporus*" by Kayo Ikeda et al., FEMS Microbiology Letters 168 (1998) 195–199.
"Intergeneric conjugation between *Escherichia coli* and Streptomyces Species" by Philippe Mazodier, et al., Journal of Bacteriology, Jun. 1989, vol. 171, No. 6, pp. 3583–3585.
"Production of copolyesters of 3–hydroxybutyrate and 3–hydroxyvalerate by Alcaligenes eutrophus from butyric and plentanoic acids" by Yoshiharu Doi et al., Applied and Microbiology (1998) 28, pp. 330–334.

* cited by examiner

Primary Examiner—Ponnathapu Achuta Murthy
Assistant Examiner—Christian L. Fronda
(74) Attorney, Agent, or Firm—Smith, Gambrell & Russell, LLP (57) ABSTRACT

The present invention relates to a process for the production of polyhydroxyoctanoate, said method involving construction of a multifunctional *Escherichia coli*—Streptomyces conjugative shuttle vector, development of a recombinant vector designated as pCAB218, which is used to transform *Streptomyces lividans* TK64, such that it is capable of producing polyhydroxyoctanoate (PHO) in substantial amounts when grown in a conventional mineral medium.

7 Claims, 3 Drawing Sheets

(1 of 3 Drawing Sheet(s) Filed in Color)

| No. | SI | MW | MF / Name |
|---|---|---|---|
| 1. | 74 | 202 | C10H18O4  Butanedioic acid, dipropyl ester (9CI) |
| 2. | 68 | 101 | C4H7NS   Thiocyanic acid, propyl ester (8CI9CI) |
| 3. | 62 | 174 | C8H14O4  Butanedioic acid, diethyl ester (9CI) |

Fig. 7c

| No. | SI | MW | MF / Name |
|---|---|---|---|
| 4. | 80 | 178 | C10H10O3  Benzeneacetic acid, .alpha.-oxo-, ethyl ester (9CI) |
| 5. | 78 | 164 | C10H12O2  Benzoic acid, 1-methylethyl ester (9CI) |
| 6. | 77 | 210 | C14H10O2  Ethanedione, diphenyl- (9CI) |

SEQUENCE LISTING

<160> NUMBER OF SEQ ID NOS: 2

<210> SEQ ID NO 1
<211> LENGTH: 12738
<212> TYPE: DNA
<213> ORGANISM: Streptomyces lividans

<400> SEQUENCE: 1

| | | | | | |
|---|---|---|---|---|---|
| ggtaccgcct | gcacgaagtg | ccggcggggc | cgaccccggg | cgagtaatcc | caggattact | 60 |
| cccgcggctt | cgaccccggc | cgccgtcgcc | gcgtacgtca | ccgaccccg | ccgtacgtca | 120 |
| ccgggatgac | gtacggcggg | ggggagcgag | ttagtgcgaa | gtgggcccac | ttgcgagccg | 180 |
| ggcgatgtgc | cgggcggccc | gctcctggcg | gtcgtcggcg | tcgtcgtcct | ggtcgtcgtc | 240 |
| ctgctctcgc | cgtcggcgtg | cagttgcttc | ctcgcggcgc | tgggcgaggg | cggcgagcat | 300 |
| gtcggcgtac | gcctcggcca | cctcccccgc | cgtgagcacc | accactgtgt | cggccgcgtc | 360 |
| ggccagcgcc | aggacctccc | gcacccgttc | gcccacggcc | gccggatcct | cgttgccgtc | 420 |
| cttgccttcg | gcgcccggg | tcgcctcgag | gtcgagggcg | cggcgggtga | ccgcgtgcca | 480 |
| tccgtcctcg | gtcacggcga | ccccggcccg | cagctcccg | ccgtcggcgt | cggccgccag | 540 |
| gagcagatcg | aggtcgtcgg | cctcggtgtc | gccgccgtca | gcccgagca | tctgccgcag | 600 |
| gtagcgggtc | cattcgatgg | cccggcgtcc | ccggggttgcc | cgctcgtact | cgtgccagcg | 660 |
| cgagaggttc | cactccagcg | agccgacccc | ggcggcgtcc | tcctcggtca | tgccgccggt | 720 |
| caggtccccg | atccgtccga | ggagttcgaa | cggggcgacg | ttcccgccgg | tcgccgtctt | 780 |
| gaggtcggcg | cgggcgagtt | cgagggcggg | cgccttcccg | tcctgggtct | tggcgatgta | 840 |
| ctcggcgagg | tcgttggcgt | cgcgctcggt | ctccagccgc | ttgaagtcga | cgccgtgccg | 900 |
| gtcgtcgggc | gtgaaggcgg | ggttgacctt | gcgcagggcg | gcggtccaca | cggaccgcca | 960 |
| gtgcccctgc | cactcgtcga | gcgcggcgcc | ggtcggctcg | aaggtggcga | cgatctgctt | 1020 |
| cgcggaccgc | tccccctcgg | tccggccgcc | gaccaggacg | atcgcgtgga | tgtgcgggtg | 1080 |
| ccagccgttg | atctgcccca | cggtgacttc | ggtcgcgcgg | atcatgccga | cgtacccgat | 1140 |
| ccggtctcga | tgccctcgc | ggtcggcggc | cggtgcccg | tccttggccc | ggcgtccggc | 1200 |
| ccacgtgccg | cccgtgatca | gtcgctggta | ggcgcccggc | cgccggggc | tgtccggcgt | 1260 |
| cttccgggtg | ccctggaggg | cgtccatgag | gtccgcgagc | cggtccgtgt | gcccatggcg | 1320 |
| ggccgtgaag | gtgaccaggt | aggcggtccc | ccgcgcttg | atccactcga | ccacggcggc | 1380 |
| ggtgatctcc | tcggcccgct | tgtgccggat | cgtggcggcg | cagaccgggc | agagccagat | 1440 |
| ccgcccgcac | cgcatcaggc | ccaggaccac | ggacgttccg | gccgccgtct | gggcgacgat | 1500 |
| cacgccggag | gcagggtcca | tcagggcgcg | gccgcagccc | ttgcacgcgg | cgtcccgct | 1560 |
| gatccgccac | agcgtccggc | ggcggctgta | ccgggcggct | ttccgcagtc | gggcagcctc | 1620 |
| ggtccgcgac | gtgcttccta | cttcccagag | gctgtcgcct | ctcgggctct | ccccatccac | 1680 |
| cccgtccgga | gaaaccgcag | gtcggagggg | tgcgggaaac | tctgttgttt | ctttcccaag | 1740 |
| gtgttcgctt | ttgcctcggg | cggcatctcg | cgtcacacgc | gcgatcgccc | gcttcgctgc | 1800 |
| catccggcag | cggtctgagc | agtagatacg | cggccgtttg | cccggtgtgt | gggcaattgc | 1860 |
| ggtcccgcag | tggcagcggg | gcccggcggg | ccgatctggc | aatgcctcgg | catcgctccg | 1920 |
| tactctgggc | acgagcaacg | ttcctgtctc | gcccggctaa | ggggcgcgag | tctgggagcg | 1980 |
| gacgggtcgg | aggtgcgaag | tccggcccgt | tgctctttgg | tctggtggga | atcctggcac | 2040 |

-continued

```
caatcgggcc agaggttccc tccgccactc ccgacgcccc ttggggctgg tgtgacttgg    2100
agggccgaag agagccccgc cgggtatccg gcggggcttt gacgtgcggt cagtgcgtgt    2160
gtcggcgagc gatggccacg aggccctgga agccgagcgg tccggcgaag tcggcccagt    2220
cgcaaccggg ctcagcgcag tgggcggacc agccaccgcc gttggggtcc tggaccaggt    2280
tcacggtccc ctcggtcagg cgtccgtcga agtcggtcat ggtcggtctc ctggtgggtg    2340
ggggcggggc gccagcacga agtgccggcg ccccgcgggg gttggtcggg tcaggcgccg    2400
aaccggcggg cggcggcggc gaccaggccg tcggcggcg ccatggcgcg gtcgcggtcg    2460
gtggtgaggg cggtgcggtc ggcggcggcc cgcaggtcgt aggccgcttg gcggcggcg    2520 gtcgctgcgg gggcgaggc gggggcgagc accgacacgt tggtgagggg cgcggtgatc    2580
gcggagcggg tggcgtggga ctcggtgcgg gccgcctcgt acgcctcggg ggaggcgccg    2640
gtcaggcgca ggtcctcgcg cactgatcaa ggcgaatact tcatatatgc ggggatcgac    2700
cgcgcgggtc ccggacgggg aagagcgggg agctttgcca gagagcgacg acttcccctt    2760
gcgttggtga ttgccggtca gggcagccat ccgccatcgt cgcgtagggt gtcacacccc    2820
aggaatcgcg tcactgaaca cagcagccgg taggacgacc atgactgagt tggacaccat    2880
cgcaaatccg tccgatcccg cggtgcagcg gatcatcgat gtcaccaagc cgtcgcgatc    2940
caacataaag acaacgttga tcgaggacgt cgagcccctc atgcacagca tcgcggccgg    3000
ggtggagttc atcgaggtct acggcagcga cagcagtcct tttccatctg agttgctgga    3060
tctgtgcggg cggcagaaca taccggtccg cctcatcgac tcctcgatcg tcaaccagtt    3120
gttcaagggg gagcggaagg ccaagacatt cggcatcgcc cgcgtccctc gcccggccag    3180
gttcggcgat atcgcgagcc ggcgtgggga cgtcgtcgtt ctcgacgggg tgaagatcgt    3240
cgggaacatc ggcgcgatag tacgcacgtc gctcgcgctc ggagcgtcgg ggatcatcct    3300
ggtcgacagt gacatcacca gcatcgcgga ccggcgtctc caaagggcca gccgaggtta    3360
cgtcttctcc cttcccgtcg ttctctccgg tcgcgaggag gccatcgcct tcattcggga    3420
cagcggtatg cagctgatga cgctcaaggc ggatggcgac atttccgtga aggaactcgg    3480
ggacaatccg gatcggctgg ccttgctgtt cggcagcgaa aagggtgggc cttccgacct    3540
gttcgaggag gcgtcttccg cctcggtttc catccccatg atgagccaga ccgagtctct    3600
caacgttccc gtttccctcg gaatcgcgct gcacgagagg atcgacagga atctcgcggc    3660
caaccgataa gcgcctctgt tcctcggacg ctcggttcct cgacctcgat tcgtcagtga    3720
tccccgcaaa agcggccttt gactccctgc aagcctcagc gaccgaatat atcggttatg    3780
cgtgggcgat ggttgttgtc attgtcggcg caactatcgg tatcaagctg tttaagaaat    3840
tcacctcgaa agcaagctga taaaccgata caattaaagg ctccttttgg agcctttttt    3900
tttggagatt ttcaacgtga aaaattatt attcgcaatt cctttagttg ttcctttcta    3960
ttctcactcc gctgaaactg ttgaaagttg tttagcaaaa cctcatacag aaaattcatt    4020
tactaacgtc tggaaagacg acaaaacttt aagctttcgc gcgtttcggt gatgacggtg    4080
aaaacctctg acacatgcag ctcccggaga cggtcacagc ttgtctgtaa gcggatgccg    4140
ggagcagaca agcccgtcag ggcgcgtcag cgggtgttgg cgggtgtcgg ggctggctta    4200
actatgcggc atcagagcag attgtactga gagtgcacca tatgcggtgt gaaataccgc    4260
acagatgcgt aaggagaaaa taccgcatca ggcgccattc gccattcagg ctgcgcaact    4320
gttgggaagg gcgatcggtg cgggcctctt cgctattacg ccactgcatt aatgaatcgg    4380
```

-continued

```
ccaacgcgcg gggagaggcg gtttgcgtat tgggcgctct tccgcttcct cgctcactga    4440
ctcgctgcgc tcggtcgttc ggctgcggcg agcggtatca gctcactcaa aggcggtaat    4500
acggttatcc acagaatcag gggataacgc aggaaagaac atgtgagcaa aaggccagca    4560
aaaggccagg aaccgtaaaa aggccgcgtt gctggcgttt ttccataggc tccgcccccc    4620
tgacgagcat cacaaaaatc gacgctcaag tcagaggtgg cgaaacccga caggactata    4680
aagataccag gcgtttcccc ctggaagctc cctcgtgcgc tctcctgttc cgaccctgcc    4740
gcttaccgga tacctgtccg cctttctccc ttcgggaagc gtggcgcttt ctcatagctc    4800
acgctgtagg tatctcagtt cggtgtaggt cgttcgctcc aagctgggct gtgtgcacga    4860
accccccgtt cagcccgacc gctgcgcctt atccggtaac tatcgtcttg agtccaaccc    4920
ggtaagacac gacttatcgc cactggcagc agccactggt aacaggatta gcagagcgag    4980
gtatgtaggc ggtgctacag agttcttgaa gtggtggcct aactacggct acactagaag    5040
gacagtattt ggtatctgcg ctctgctgaa gccagttacc ttcggaaaaa gagttggtag    5100
ctcttgatcc ggcaaacaaa ccaccgctgg tagcggtggt ttttttgttt gcaagcagca    5160
gattacgcgc agaaaaaaag gatctcaaga agatcctttg atcttttcta cggggtctga    5220
cgctcagtgg aacgaaaact cacgttaagg gattttggtc atgagattat caaaaaggat    5280
cttcacctag atccttttaa attaaaaatg aagttttaaa tcaatctaaa gtatatatga    5340
gtaaacttgg tctgacagtt accaatgctt aatcagtgag gcacctatct cagcgatctg    5400
tctatttcgt tcatccatag ttgcctgact ccccgtcgtg tagataacta cgatacggga    5460
gggcttacca tctggcccca gtgctgcaat gataccgcga gacccacgct caccggctcc    5520
agatttatca gcaataaacc agccagccgg aagggccgag cgcagaagtg gtcctgcaac    5580
tttatccgcc tccatccagt ctattaattg ttgccgggaa gctagagtaa gtagttcgcc    5640
agttaatagt ttgcgcaacg ttgttgccat tgctacaggc atcgtggtgt cacgctcgtc    5700
gtttggtatg gcttcattca gctccggttc ccaacgatca aggcgagtta catgatcccc    5760
catgttgtgc aaaaaagcgg ttagctcctt cggtcctccg atcgttgtca gaagtaagtt    5820
ggccgcagtg ttatcactca tggttatggc agcactgcat aattctctta ctgtcatgcc    5880
atccgtaaga tgcttttctg tgactggtga gtactcaacc aagtcattct gagaatagtg    5940
tatgcggcga ccgagttgct cttgcccggc gtcaatacgg gataataccg cgccacatag    6000
cagaacttta aaagtgctca tcattggaaa acgttcttcg gggcgaaaac tctcaaggat    6060
cttaccgctg ttgagatcca gttcgatgta acccactcgt gcacccaact gatcttcagc    6120
atcttttact ttcaccagcg tttctgggtg agcaaaaaca ggaaggcaaa atgccgcaaa    6180
aaagggaata agggcgacac ggaaatgttg aatactcata ctcttccttt ttcaatatta    6240
ttgaagcatt tatcagggtt attgtctcat gagcggatac atatttgaat gtatttagaa    6300
aaataaacaa ataggggttc cgcgcacatt tccccgaaaa gtgccacctg acgtctaaga    6360
aaccattatt atcatgacat taacctataa aaataggcgt atcacgaggc cctttcgtca    6420
agcttctaga ctggcgaaag ggggatgtgc tgcaaggcga ttaagttggg taacgccagg    6480
gttttcccag tcacgacgtt gtaaaacgac ggccagtgaa ttctcggcgc tgacaccat    6540 acatgtggcc caggctgcgt cattccggcg cggtcgcggc tccggcagg ccttccagga    6600 cccgctctat ctccagcgag tcctgcatgc gccggatggc cgcatgcagt tcggcggcct    6660
gtggccaggt ccgcttgaaa tagctgagcc acagtttcac gcgcccatgc tcatggcacg    6720
acgcgatacg ggcctgcagc ctcgccccg cgagggccgc gctgcacgaa catggtgctg    6780
```

```
gctgcgccgc tgccctgatt ctatgcccaa caaggcacta agaaaagcga cggggcttaa    6840
ggaaaacccg gtgaattggc gcaaaaagcg aggaatgccg cgcgggcaga acgattcgc    6900 gggccttgac ggcccgcgaa acgggcggcg aaacgaaacg cccgccgcct tgtgcgccgc    6960
gctggctgca ccgcaatacg cgggcgccag cgccggctgc cgactggttg aaccaggccg    7020
gcaggtcagc ccatatgcag gccgccgttg agcgagaagt cggcgccggt cgagaaaccg    7080
gactcctccg acgacaacca ggcgcagatc gaggcgatct cttccggcag gcccaggcgc    7140
ttgaccggga tcgtcgcgac gatcttgtcg agcacgtcct ggcggatcgc cttgaccatg    7200
tcggtggcga tatagcccgg agagaccgtg ttgacggtca cgcccttggt cgccacttcc    7260
tgcgccagtg ccatggtgaa gccatgcagg ccggccttgg cggtggagta gttggtctgg    7320
ccgaactggc ccttctgccc gttcaccgac gagatgttga cgatgcggcc ccagccacgg    7380
tcggccatgc cgtcgatcac ctgcttggtg acgttgaaca gcgaggtcag gttggtgtcg    7440
atcaccgcat cccagtcggc gcgggtcatc ttgcggaaca ccacgtcgcg ggtgataccg    7500
gcgttgttga tcagcacatc aacctcgccg acctcggact tgaccttgtc gaatgcggtc    7560
ttggtcgagt cccagtcagc cacattgcct tccgaggcaa tgaaatcgaa gcccagggcc    7620
ttctgctgct ccagccactt ttcgcggcgc ggcgagttgg ggccgcaacc ggccaccaca    7680
cgaaagccat ccttggccag ccgctggcaa atggcggttc cgataccacc catgccgccg    7740
gtcacatacg caatgcgctg agtcatgtcc actccttgat tggcttcgtt atcgtcgccg    7800
ggtccgcgcc aaccgcgcgc ggccccggaa accccttcc ttatttgcgc tcgactgcca    7860
gcgccacgcc catgccgccg ccgatgcaca gcgaggccag gcccttcttc gcgtcacggc    7920
gcttcatctc gtgcagcagc gtcaccagga tacggcagcc cgacgcgccg atcgggtggc    7980
cgatggcgat ggcgccgccg ttcacattga ccttggaggt gtcccagccc atctgctggt    8040
gcaccgccag cgcctgcgcg gcaaaggcct cgttgatctc catcaggtcc aggtcttgcg    8100
gggtccactc ggcgcgcgac agggcgcgct tggaggccgg caccgggccc atgcccatca    8160
ccttgggatc gacaccggcg ttggcatagc tcttgatcgt ggccagcggg gtcaggccca    8220
gttccttggc cttggccgcc gacatcacca ccaccgcggc ggcgccgtcg ttcaggcccg    8280
aggcgttggc gcggtcacc gtgccggcct tgtcgaaggc gggcttgagg ccggacatgc    8340
tgtccagcgt ggcgccctgg cgcacgaact cgtcggtctt gaaggccacc gggtcgccct    8400
tgcgctgcgg gatcagcacc gggacgatct cttcgtcaaa cttgccggcc ttctgcgcgg    8460
cttcggcctt gttctgcgag ccgacggcga actcatcctg cgcctcgcgt gtgatgccgt    8520
attccttggc cacgttctcg gcggtgatgc ccatgtggta ctggttgtac acgtcccaca    8580
ggccgtcgac gatcatggtg tcgaccagct tggcatcgcc catgcggaaa ccatcgcgcg    8640
agcccggcag cacgtgcggg gcggcgctca tgttttcctg gccgccggcc accacgatct    8700
cggcgtcgcc cgccatgatc gcgttggcgg ccagcatcac ggccttcagg cccgagccgc    8760
acaccttgtt gatggtcatg gccggcacca tcgccggcag gccggccttg atcgcggcct    8820
ggcgtgcggg gttctggccc gaaccggcgg tcagcacctg gcccatgatg acttcgctca    8880
cctgctccgg cttgacgccg gcgcgctcca gcgcggcctt gatgaccacg gcacccagtt    8940
ccggtgccgg gatcttggcc agcgagccgc caaacttgcc gaccgcggtg cgggcggcgg    9000
atacgatgac aacgtcagtc attgtgtagt cctttcaatg gaaacgggag ggaacctgca    9060
ggcctgccgg cgccgtgcat gacgcacgcc ggcactcatg caagcgtcat gccttggctt    9120
```

-continued

| | | | | |
|---|---|---|---|---|
| tgacgtatcg | cccaggcgcg | ggttcgattg | cgcgatagcg | cgcattgcca tagttggcgg | 9180 |
| gcgcggcgcg | tttcgcgccg | gcctgcccgg | ccagccatgc | ggtccagtcc ggccaccagc | 9240 |
| tgccgtgatg | ctcgatggcg | ccggccagcc | attgctgcgg | cgactccggc agcgcatcgt | 9300 |
| tagtccagtg | gctgcgcttg | ttcttggccg | gcgggttgat | cacaccggcg atatggcccg | 9360 |
| acgcacccag | cacgaagcgc | agcttgttcg | ccagcagcgc | ggtcgaggca taggccgcg | 9420 |
| tccacggcac | gatatggtct | tcgcgcgagc | cgtagatata | ggtcggcacg tcgatgctgg | 9480 |
| ccaggtccac | cggcacgccg | cacacggtca | gcttgcccgg | taccttgagc tcgttctgca | 9540 |
| ggtaggtgtg | gcgcaggtac | cagcagtacc | acggccccgg | caggttggtg gcgtcgccgt | 9600 |
| tccagaacag | caggtcgaac | ggcaccggcg | tgttgccctt | caggtagttg tcgaccacgt | 9660 |
| agttccacac | caggtcgttc | gggcgcaaga | acgagaaggt | attggccagc tcaaggccgc | 9720 |
| gcagcagcgc | gcacggcgcg | ccggcgccg | cgcccagcgt | ggcctcgcgc aactgcacat | 9780 |
| ggccctcgtc | gacaaagacg | tcgaggatgc | ccgtgtcggc | aaagtccagc agcgtggtca | 9840 |
| gcagcgtgac | gctggcggcc | gggtgctcgc | cgcgcgcggc | cagcaccgcc agcgcggtcg | 9900 |
| agacaatggt | gccgcccacg | cagaagccga | gcacgttgat | cttgtcctgg ccgctgatgt | 9960 |
| cgcgcgcgac | ttcgatggcg | cggatggccg | cgtgctcgat | gtagtcgtcc caggtgctgc | 10020 |
| cggccatgct | ggcgtccgga | ttgcgccacg | acaccagaaa | caccgtatgt ccctgctcca | 10080 |
| ccacatggcg | caccagcgag | ctctccggct | gcaggtccag | gatgtagtac ttgttgatgc | 10140 |
| acggcggcac | catcagcagc | gggcgcgcgt | gcaccttgtc | ggtcagcggc ttgtactgca | 10200 |
| acagctggaa | gtactcgttc | tcgaagacca | cggcgcctc | ggtcaccgcg acattgcggc | 10260 |
| cgacctcaaa | cgcgctctcg | tcggtctgcg | agatcttgcc | gcgtgtcagg tcttccatca | 10320 |
| tgttgcgcac | gccggcacgc | agcgattcgc | cgcccgactc | gatcagcagg cgctgcgcct | 10380 |
| cgggattggt | ggcaaggaag | ttggcgggcg | acatcgcatc | gacccattgc gagatcgcga | 10440 |
| agcggatgcg | ctggcgggtc | ttggcatcgg | cctcgacggc | atcggccagc tcggtcaagg | 10500 |
| cgcgcgcatt | gagcaggtag | aacgcggcag | cgaagcgata | tgggaggttg gtgcgccatg | 10560 |
| cgtcgccggc | gaagcgccgg | tcgtgcagcg | gaccggtggc | ctcggccttg ccctcggcca | 10620 |
| tggcctgcca | cagcgctgag | aagtccttca | tgtagcgctg | ctggatatca cccagctgcg | 10680 |
| ccggcgcgat | cttgacgcct | gccagcgcat | ccaggcccgg | aatgccggac gcggccgcgt | 10740 |
| ggccgttgcc | ttcagtgccc | tgccactggc | gggaccattc | cagccatgtg gctggatcga | 10800 |
| atggccccgg | cgtgaccttg | aatggttggg | acttgccttc | ctgcgtggaa gctgccgcgc | 10860 |
| ctttgccggt | cgccatgatt | tgattgtctc | tctgccgtca | ctattcgaac cggctccggg | 10920 |
| cattgccctg | gccggcactt | tgcatgggga | gatgctatcc | gaatggaccc ggcttgcgcc | 10980 |
| tcccccaaag | cgggagggtc | tgccggcaca | tctgccctgg | aactggctgg aagccctcga | 11040 |
| ccgcacctgc | tgcggccgtg | gcttgcgtcc | attccgatag | cggctcccct tttatccggc | 11100 |
| aagcgcgaca | ttctcgcatg | gagacgccat | gcgctatgct | tgccggagaa acctgggaat | 11160 |
| cgtcagcgat | tccgagacat | ttgagtccat | tgttgccttg | caacgcacgc gctgtcaatg | 11220 |
| cgggaatccg | cctcggcact | gcacgcttcc | cgacctaccg | gacggtatgc agcgctcgca | 11280 |
| tctgccgagg | ccccagagca | taggcgagaa | ggatgaattt | ttgatgtaca tcgtggccat | 11340 |
| tggctggctc | tacgtggcgc | tgatgatggc | gatcaccgag | cacaacgtgg tggcaggcgt | 11400 |
| tgccaccttc | ctgatgtatg | gcatggcgcc | ggtggcgtgg | tgctctacat catgggcacg | 11460 |
| cccggccgcc | gccgacgcaa | ggctgaagcc | gagcgcgcgc | aggcggccag gggcaaggac | 11520 |

-continued

```
gagtgaggca gcggcgggct cagtccgcca gccagaccag gctggccatg cggccggtca    11580
cgccatcgcg ccgataggag tagaagcgac cggcgtcggc cacggtgcag gcgtcgccgc    11640
cgtagacctc ggtacagccg gcgcgcgcca ggcgcgtgcg cgccagcgca tagatgtcgg    11700
caaggtactt gcccggggat cctctagagt cgacctgcac tgcaggtcga cggatctttt    11760
ccgctgcata accctgcttc ggggtcatta tagcgatttt tcggtatat ccatccttt     11820 tcgcacgata tacaggattt tgccaaaggg ttcgtgtaga ctttccttgg tgtatccaac    11880
ggcgtcagcc gggcaggata ggtgaagtag gcccaccgc gagcgggtgt tccttcttca    11940
ctgtccctta ttcgcacctg gcggtgctca acgggaatcc tgctctgcga ggctggccgg    12000
ctaccgccgg cgtaacagat gagggcaagc ggatggctga tgaaaccaag ccaaccagga    12060
agggcagccc acctatcaag gtgtactgcc ttccagacga acgaagagcg attgaggaaa    12120
aggcggcggc ggccggcatg agcctgtcgg cctacctgct ggccgtcggc cagggctaca    12180
aaatcacggg cgtcgtggac tatgagcacg tccgcgagct ggcccgcatc aatggcgacc    12240
tgggccgcct gggcggcctg ctgaaactct ggctcaccga cgacccgcgc acggcgcggt    12300
tcggtgatgc cacgatcctc gccctgctgg cgaagatcga agagaagcag gacgagcttg    12360
gcaaggtcat gatgggcgtg gtccgcccga gggcagagcc atgactttt tagccgctaa     12420 aacggccggg gggtgcgcgt gattgccaag cacgtcccca tgcgctccat caagaagagc    12480
gacttcgcgg agctggtgaa gtacatcacc gacgagcaag gcaagaccga tccccgggga    12540
cctgcagggc atgcaagctt ggcgtaatca tggtcatagc tgtttcctgt gtgaaattgt    12600
tatccgctca caattccaca caacatacga gccgaagca taaagtgtaa agcctggggt     12660
gcctaatgag tgagctaact cacattaatt gcgttgcgct cactgcccgc tttccagtcg    12720
ggaaacctgt cgtgccag                                                  12738
```

<210> SEQ ID NO 2
<211> LENGTH: 7560
<212> TYPE: DNA
<213> ORGANISM: Streptomyces lividans

<400> SEQUENCE: 2

```
ggtaccgcct gcacgaagtg ccggcggggc cgaccccggg cgagtaatcc caggattact     60
cccgcggctt cgaccccggc cgccgtcgcc gcgtacgtca ccgaccccg ccgtacgtca     120 ccgggatgac gtacggcggg gggagcgag ttagtgcgaa gtgggcccac ttgcgagccg    180
ggcgatgtgc cggcggccc gctcctggcg gtcgtcggcg tcgtcgtcct ggtcgtcgtc    240
ctgctctcgc cgtcggcgtg cagttgcttc ctcgcggcgc tgggcgaggg cggcgagcat    300
gtcggcgtac gcctcggcca cctcccccgc cgtgagcacc accactgtgt cggccgcgtc    360
ggccagcgcc aggacctccc gcacccgttc gcccacggcc gccggatcct cgttgccgtc    420
cttgccttcg gcggcccggg tcgcctcgag gtcgagggcg cggcgggtga ccgcgtgcca    480
tccgtcctcg gtcacggcga ccccggcccg cagctccccg ccgtcggcgt cggccgccag    540
gagcagatcg aggtcgtcgg cctcggtgtc gccgccgtcg agcccgagca tctgccgcag    600
gtagcgggtc cattcgatgg cccggcgtcc ccggttgcc cgctcgtact cgtgccagcg     660
cgagaggttc cactccagcg agccgacccc ggcggcgtcg tcctcggtca tgccgccggt    720
caggtccccg atccgtccga ggagttcgaa cggggcgacg ttcccgccgg tcgccgtctt    780
gaggtcggcg cgggcgagtt cgagggcggg cgccttcccg tcctgggtct tggcgatgta    840
```

```
ctcggcgagg tcgttggcgt cgcgctcggt ctccagccgc ttgaagtcga cgccgtgccg    900
gtcgtcgggc gtgaaggcgg ggttgacctt gcgcagggcg gcggtccaca cggaccgcca    960
gtgcccctgc cactcgtcga gcgcggcgcc ggtcggctcg aaggtggcga cgatctgctt   1020
cgcggaccgc tcccctcgg tccggccgcc gaccaggacg atcgcgtgga tgtgcgggtg   1080
ccagccgttg atctgcccca cggtgacttc ggtcgcgcgg atcatgccga cgtacccgat   1140
ccggtctcgg atgccctcgc ggtcggcggc ccggtgcccg tccttggccc ggcgtccggc   1200
ccacgtgccg cccgtgatca gtcgctggta ggcgcccggc cgccggggc tgtccggcgt    1260 cttccgggtg ccctggaggg cgtccatgag gtccgcgagc cggtccgtgt gcccatggcg   1320
ggccgtgaag gtgaccaggt aggcggtccc ccgcgcttg atccactcga ccacggcggc   1380
ggtgatctcc tcggcccgct tgtgccggat cgtggcggcg cagaccgggc agagccagat   1440
ccgcccgcac cgcatcaggc ccaggaccac ggacgttccg gccgccgtct gggcgacgat   1500
cacgccggag gcagggtcca tcaggcgcg gccgcagccc ttgcacgcgg cgtccccgct    1560
gatccgccac agcgtccggc ggcggctgta ccgggcggct ttccgcagtc gggcagcctc   1620
ggtccgcgac gtgcttccta cttcccagag gctgtcgcct ctcgggctct ccccatccac   1680
cccgtccgga gaaaccgcag gtcggagggg tgcgggaaac tctgttgttt ctttcccaag   1740
gtgttcgctt ttgcctcggg cggcatctcg cgtcacacgc gcgatcgccc gcttcgctgc   1800 catccgcag cggtctgagc agtagatacg cggccgtttg cccggtgtgt gggcaattgc    1860
ggtcccgcag tggcagcggg gcccggcggg ccgatctggc aatgcctcgg catcgctccg   1920
tactctgggc acgagcaacg ttcctgtctc gcccggctaa ggggcgcgag tctgggagcg   1980
gacgggtcgg aggtgcgaag tccggccgt tgctctttgg tctggtggga atcctggcac    2040
caatcgggcc agaggttccc tccgccactc ccgacgcccc ttggggctgg tgtgacttgg   2100
agggccgaag agagccccgc cgggtatccg gcggggcttt gacgtgcggt cagtgcgtgt   2160
gtcggcgagc gatggccacg aggccctgga agccgagcgg tccggcgaag tcggcccagt   2220
cgcaaccggg ctcagcgcag tgggcggacc agccaccgcc gttggggtcc tggaccaggt   2280
tcacggtccc ctcggtcagg cgtccgtcga agtcggtcat ggtcggtctc ctggtgggtg   2340
ggggcggggc gccagcacga agtgccggcg ccccgcgggg gttggtcggg tcaggcgccg   2400
aaccggcggg cggcggcggc gaccaggccg tcggcggcgg ccatggcgcg gtcgcggtcg   2460
gtggtgaggg cggtgcggtc ggcggcggcc cgcaggtcgt aggccgcttg ggcggcggcg   2520
gtcgctgcgg gggcgagggc ggggcgagc accgacacgg tggtgagggg cgcggtgatc   2580
gcggagcggg tggcgtggga ctcggtgcgg gccgcctcgt acgcctcggg ggaggcgccg   2640
gtcaggcgca ggtcctcgcg cactgatcaa ggcgaatact tcatatatgc ggggatcgac   2700
cgcgcgggtc ccggacgggg aagagcgggg agctttgcca gagagcgacg acttcccctt   2760
gcgttggtga ttgccggtca gggcagccat ccgccatcgt cgcgtagggt gtcacacccc   2820
aggaatcgcg tcactgaaca cagcagccgg taggacgacc atgactgagt tggacaccat   2880
cgcaaatccg tccgatcccg cggtgcagcg gatcatcgat gtcaccaagc cgtcgcgatc   2940
caacataaag acaacgttga tcgaggacgt cgagcccctc atgcacagca tcgcggccgg   3000
ggtggagttc atcgaggtct acggcagcga cagcagtcct tttccatctg agttgctgga   3060
tctgtgcggg cggcagaaca taccggtccg cctcatcgac tcctcgatcg tcaaccagtt   3120
gttcaagggg gagcggaagg ccaagacatt cggcatcgcc cgcgtccctc gcccggccag   3180
gttcggcgat atcgcgagcc ggcgtgggga cgtcgtcgtt ctcgacgggg tgaagatcgt   3240
```

```
cgggaacatc ggcgcgatag tacgcacgtc gctcgcgctc ggagcgtcgg ggatcatcct    3300
ggtcgacagt gacatcacca gcatcgcgga ccggcgtctc caaagggcca gccgaggtta    3360
cgtcttctcc cttccgtcg ttctctccgg tcgcgaggag gccatcgcct tcattcggga     3420
cagcggtatg cagctgatga cgctcaaggc ggatggcgac atttccgtga aggaactcgg    3480
ggacaatccg gatcggctgg ccttgctgtt cggcagcgaa aagggtgggc cttccgacct    3540
gttcgaggag gcgtcttccg cctcggtttc catccccatg atgagccaga ccgagtctct    3600 caacgttttcc gtttccctcg gaatcgcgct gcacgagagg atcgacagga atctcgcggc    3660
caaccgataa gcgcctctgt tcctcggacg ctcggttcct cgacctcgat tcgtcagtga    3720
tccccgcaaa agcggccttt gactccctgc aagcctcagc gaccgaatat atcggttatg    3780
cgtgggcgat ggttgttgtc attgtcggcg caactatcgg tatcaagctg tttaagaaat    3840
tcacctcgaa agcaagctga taaaccgata caattaaagg ctccttttgg agcctttttt    3900
tttggagatt ttcaacgtga aaaattatt attcgcaatt cctttagttg ttcctttcta     3960
ttctcactcc gctgaaactg ttgaaagttg tttagcaaaa cctcatacag aaaattcatt    4020
tactaacgtc tggaaagacg acaaaacttt aagctttcgc gcgtttcggt gatgacggtg    4080
aaaacctctg acacatgcag ctcccggaga cggtcacagc ttgtctgtaa gcggatgccg    4140
ggagcagaca gcccgtcag ggcgcgtcag cgggtgttgg cgggtgtcgg ggctggctta    4200
actatgcggc atcagagcag attgtactga gagtgcacca tatgcggtgt gaaataccgc    4260
acagatgcgt aaggagaaaa taccgcatca ggcgccattc gccattcagg ctgcgcaact    4320
gttgggaagg cgatcggtg cgggcctctt cgctattacg ccactgcatt aatgaatcgg     4380
ccaacgcgcg gggagaggcg gtttgcgtat tgggcgctct ccgcttcct cgctcactga     4440 ctcgctgcgc tcggtcgttc ggctgcggcg agcggtatca gctcactcaa aggcggtaat    4500
acggttatcc acagaatcag gggataacgc aggaaagaac atgtgagcaa aaggccagca    4560
aaaggccagg aaccgtaaaa aggccgcgtt gctggcgttt ttccataggc tccgccccc     4620 tgacgagcat cacaaaaatc gacgctcaag tcagaggtgg cgaaacccga caggactata    4680
aagataccag gcgtttcccc ctggaagctc cctcgtgcgc tctcctgttc cgaccctgcc    4740
gcttaccgga tacctgtccg cctttctccc ttcgggaagc gtggcgcttt ctcatagctc    4800
acgctgtagg tatctcagtt cggtgtaggt cgttcgctcc aagctgggct gtgtgcacga    4860 acccccgtt cagcccgacc gctgcgcctt atccggtaac tatcgtcttg agtccaaccc     4920
ggtaagacac gacttatcgc cactggcagc agccactggt aacaggatta gcagagcgag    4980
gtatgtaggc ggtgctacag agttcttgaa gtggtggcct aactacggct acactagaag    5040
gacagtattt ggtatctgcg ctctgctgaa gccagttacc ttcggaaaaa gagttggtag    5100
ctcttgatcc ggcaaacaaa ccaccgctgg tagcggtggt ttttttgttt gcaagcagca    5160
gattacgcgc agaaaaaaag gatctcaaga agatcctttg atcttttcta cggggtctga    5220
cgctcagtgg aacgaaaact cacgttaagg gattttggtc atgagattat caaaaaggat    5280
cttcacctag atccttttaa attaaaaatg aagttttaaa tcaatctaaa gtatatatga    5340
gtaaacttgg tctgacagtt accaatgctt aatcagtgag gcacctatct cagcgatctg    5400
tctatttcgt tcatccatag ttgcctgact ccccgtcgtg tagataacta cgatacggga    5460
gggcttacca tctggcccca gtgctgcaat gataccgcga acccacgct caccggctcc     5520 agatttatca gcaataaacc agccagccgg aagggccgag cgcagaagtg gtcctgcaac    5580
```

-continued

```
tttatccgcc tccatccagt ctattaattg ttgccgggaa gctagagtaa gtagttcgcc    5640
agttaatagt ttgcgcaacg ttgttgccat tgctacaggc atcgtggtgt cacgctcgtc    5700
gtttggtatg gcttcattca gctccggttc ccaacgatca aggcgagtta catgatcccc    5760
catgttgtgc aaaaaagcgg ttagctcctt cggtcctccg atcgttgtca gaagtaagtt    5820
ggccgcagtg ttatcactca tggttatggc agcactgcat aattctctta ctgtcatgcc    5880
atccgtaaga tgcttttctg tgactggtga gtactcaacc aagtcattct gagaatagtg    5940
tatgcggcga ccgagttgct cttgcccggc gtcaatacgg gataataccg cgccacatag    6000
cagaacttta aaagtgctca tcattggaaa acgttcttcg gggcgaaaac tctcaaggat    6060
cttaccgctg ttgagatcca gttcgatgta acccactcgt gcacccaact gatcttcagc    6120 atctttttact ttcaccagcg tttctgggtg agcaaaaaca ggaaggcaaa atgccgcaaa    6180
aaagggaata agggcgacac ggaaatgttg aatactcata ctcttccttt ttcaatatta    6240
ttgaagcatt tatcagggtt attgtctcat gagcggatac atatttgaat gtatttagaa    6300
aaataaacaa ataggggttc cgcgcacatt tccccgaaaa gtgccacctg acgtctaaga    6360
aaccattatt atcatgacat taacctataa aaataggcgt atcacgaggc cctttcgtca    6420
agcttctaga ctggcgaaag ggggatgtgc tgcaaggcga ttaagttggg taacgccagg    6480
gttttcccag tcacgacgtt gtaaaacgac ggccagtgaa ttcgagctcg gtacccgggg    6540
atcctctaga gtcgacctgc actgcaggtc gacggatctt ttccgctgca taaccctgct    6600
tcggggtcat tatagcgatt ttttcggtat atccatcctt tttcgcacga tatacaggat    6660
tttgccaaag ggttcgtgta gactttcctt ggtgtatcca acggcgtcag ccgggcagga    6720
taggtgaagt aggcccaccc gcgagcgggt gttccttctt cactgtccct tattcgcacc    6780
tggcggtgct caacgggaat cctgctctgc gaggctggcc ggctaccgcc ggcgtaacag    6840
atgagggcaa gcggatggct gatgaaacca agccaaccag gaagggcagc ccacctatca    6900
aggtgtactg ccttccagac gaacgaagag cgattgagga aaaggcggcg gcggccggca    6960
tgagcctgtc ggcctacctg ctggccgtcg gccaggcta caaaatcacg ggcgtcgtgg    7020
actatgagca cgtccgcgag ctggcccgca tcaatggcga cctgggccgc ctgggcggcc    7080
tgctgaaact ctggctcacc gacgacccgc gcacggcgcg gttcggtgat gccacgatcc    7140
tcgccctgct ggcgaagatc gaagagaagc aggacgagct tggcaaggtc atgatgggcg    7200
tggtccgccc gagggcagag ccatgacttt tttagccgct aaaacggccg gggggtgcgc    7260
gtgattgcca agcacgtccc catgcgctcc atcaagaaga gcgacttcgc ggagctggtg    7320
aagtacatca ccgacgagca aggcaagacc gatcccggg gacctgcagg gcatgcaagc    7380
ttggcgtaat catggtcata gctgtttcct gtgtgaaatt gttatccgct cacaattcca    7440
cacaacatac gagccggaag cataaagtgt aaagcctggg gtgcctaatg agtgagctaa    7500
ctcacattaa ttgcgttgcg ctcactgccc gctttccagt cgggaaacct gtcgtgccag    7560
```

PROCESS FOR THE PRODUCTION OF POLYHYDROXYOCTANOATE BY STREPTOMYCES LIVIDANS

FIELD OF THE INVENTION

The present invention relates to a process for the production of polyhydroxyoctanoate in substantial amounts using recombinant *Streptomyces lividans* TK64. More particularly it relates to a method involving construction of a multifunctional *Escherichia coli*—Streptomyces conjugative shuttle vector, development of a recombinant vector designated as pCAB218, which is used to transform *Streptomyces lividans* TK64, such that it is capable of producing polyhydroxyoctanoate (PHO) in substantial amounts when grown in a conventional mineral medium.

BACKGROUND OF THE INVENTION

The citations in this specification are incorporated herein by reference to form a part of this application.

Synthetic polymers have become an integral part of our day to day life. These compounds like polyvinylchloride, polyhomopropylene, polyethylene and others are produced from fossil resources. They have many desirable properties including durability and resistance to degradation. They are used to a very high extent in the packaging industry, and once their useful life is over, are partially recycled, end in landfills, or are burnt in order to eliminate the solid waste. As far as total mass of plastic waste is concerned, these nondegradable plastics accumulate in the environment at a rate of over 25 million tonnes per year [Lee S. Y., *Biotechnol. Bioeng.*, 49 (1995), 1–14]. Recently, the problems concerning the global environment and solid waste management has created much interest in the development of biodegradable plastics, which must still retain the desired properties of conventional synthetic plastics. Some of the biodegradable plastic materials under development include polyhydroxyalkanoates (PHAs), polylactides, aliphatic polyesters, polysaccharides and the copolymers and/or blends of these [Byrome, D. (ed.), (1991), *Biomaterials*: novel materials from biological sources. Stockton, N.Y. 125–213].

Prior Art Methods

During the past 10 years polyhydroxyalkanoates (PHAs) as a class of biopolymers have globally experienced a great increase in research and development efforts. These are polyesters of hydroxyalkanoates (HAs) synthesized by numerous bacteria as intracellular carbon and energy storage compounds which accumulate as cytoplasmic granular inclusions in the cells in response to nutrient limitation. Polyhydroxybutyrate (PHB), polyhydroxyvalerate (PHV) and polyhydroxybutyrate-co-valerate (PHB-V) are by far the most widely and thoroughly characterized of the PHAs [Steinbüchel, A. and Schlegel, H. G., *Mol. Microbiol.*, 5 (1991) 30–37]. The nature of the polymer is determined by the carbon source supplied in the growth medium. Thus, *Ralstonia eutropha* grown in a medium containing glucose produces PHB. The use of propionic acid/or valeric acid as the sole carbon source in the growth medium for *Chromobacterium violaceum* yields PHV [Doi, Y. Tamaki, A., Kunioka, M. and Soga, K.,*Appl. Microbiol. Biotechnol.*, 28, (1988), 330–334; Steinbüchel, A., Debzi, E. M., Marchessault, R. H. and Timm, A. *Appl. Microbiol. Biotechnol.*, 39, (1993), 443–449]. Addition of propionic acid/or valeric acid to the glucose containing growth medium leads to the production of random copolymer PHB-V by *Ralstonia eutropha* as reported by Steinbüchel, A., In Byrom, D. ed. *Biomaterials: novel materials from biological sources*. Stocton, N.Y., (1991) pp 124–213. This is possible because of the broad substrate specificity of the bacterial enzymes involved in PHA synthesis [Doi, Y. Kunioka, M., Nakamura, Y. and Soga, K., *Macromolecules*, 21, (1988),2722–2727]. The polymer synthesis is by the sequential action of three enzymes. The first enzyme of the pathway, β-ketothiolase, coded by gene phaA, catalyzes the reversible condensation of two acyl-CoA moieties to form β-ketoacyl-CoA. Acetoacetyl-CoA reductase, coded by phaB gene, subsequently reduces β-ketoacyl-CoA to D(-)-β-hydroxyacyl-CoA, which in turn is polymerized by the action of the enzyme PHA synthase, coded by phaC gene, to form PHA. In *Ralstonia eutropha*, the structural genes for PHA synthesis are organized in a single operon designated as phaCAB$_{Re}$, coding for PHA synthase, β-ketothiolase and NADPH-dependent acetoacetyl-CoA reductase respectively.

*Pseudomonas oleovorans* a Gram negative bacterium grown on aliphatic carbon sources such as alkanes, alkanols and alkanoic acids produces PHAs of various medium chain length β-hydroxyalkanoic acids [Lageween, R. G., Huisman, G. W., Preustig, H,. Ketelaar, P., Eggnik, G. and Wuholt, B. *Appl. Environ. Microbiol.*, 54, (1988), 2924–2932]. The drawback is that this organism needs to be cultivated on octanoic acid, a very expensive aliphatic acid, to produce a homopolymer of β-hydroxyoctanoate [Timm, A., Wiese, S. and Steinbüchel, A. *Appl. Microbiol. Biotechnol.*, 40 (1994) 669–675]. There are, however, no reports suggesting the use of an alternative and cheap carbon source for the production of polyhydroxyoctanoate (PHO) by any microorganism.

Non-pathogenic soil bacteria Streptomyces species are well known for their ability to synthesize antibiotics [Berdy, J., *Process Biochem.*, October/November(1980) 28–35]. These are also reported to synthesize and accumulate polyhydroxyalkanoates (PHAs) in very small quantities [Kannan, L. V. and Rehacek, Z., *Ind. J. Biochem.*, 7 (1970) 126–129].

Applications of recombinant DNA technology in Streptomyces are on the rise [Yang, R., Hu, Z., Deng, Z. and Li, J., *Shengwu Gongcheng Xuebao*, 14 (1998) 6–12; Ikeda, K., Suzuki, K., Yoshioka, H., Miyamoto, K., Masujima, T. and Sugiyama, M., *FEMS Microbiol. Lett.*, 168 (1998) 196–199]. Since the fermentation technology is well worked out with Streptomyces species, it is desirable to exploit *Streptomyces lividans* TK64 for the production of polyhydroxyoctanoate (PHO) using an alternate and cheap carbon source. This will, however, require genetic modification of the organism. The basic DNA constructions, gene modifications and genetic manipulations will have to be first made in *Escherichia coli*, and later introduced into the Streptomyces species. This necessitates the design, construction and preparation of multifunctional shuttle or conjugative plasmid vectors which allow assembly, construction and cloning of genes along with their regulatory sequences in *Escherichia coli* and later introduction into the Streptomyces species by polyethylene glycol (PEG) mediated DNA uptake [Hopwood, D. A., Bibb, M. I., Chater, K. F., Kieser, T., Bruton, C. J., Kieser, H. M., Lydiate, D. J., Smith, C. P., Ward, J. M. and Scrempf, H., *Genetic Manipulation Of Streptomyces; A Laboratory Manual*. John Innes Foundation, Norwich, England, 1985] or through conjugation with *Escherichia coli*[Mazodier, P., Petter, R. and Thompson, C., *J.Bacteriol.*, 171 (1989) 3583–3585].

The drawback of the most often used *Escherichia coli*—Streptomyces sp. shuttle vectors is the lack of their conjugative capability [Wehmeier, U. F., *Gene*, 165 (1995) 149–150; Morino, T. and Takahashi, H., *Actinomycetologica*, 12 (1998) 37–39]. The PEG mediated transformation of Streptomyces species also suffers from the drawback of low frequency of transformation when plasmid DNA of *Escherichia coli* origin is used [Rao, R. N., Richardson, M. A. and Kuhstoss, S. A. *Methods Enzymol*, 153 (1987) 166–198]. The available *Escherichia coli*—Streptomyces sp. conjugative vectors suffer from the drawback of providing only one or two unique restriction endonuclease cloning sites thus severely limiting cloning options [Mazodier, P., Petter, R. and Thompson, C., *J.Bacteriol.*, 171 (1989) 3583–3585; Voeykova, T., Emelyanova, L., Tabakov, V. and Mkrtumyan, N., FEMS *MicroBiol. Lett.*, 162 (1998) 47–52].

Thus, there is a need in the prior art to develop a method whereby polyhydroxy octanoate can be readily and efficiently produced using *Escherichia coli*. To overcome the aforementioned drawbacks in the prior art, the applicants have designed, constructed and prepared multifunctional *Escherichia coli*—Streptomyces sp. conjugative shuttle plasmid vector which will provide multiple restriction sites for cloning ease and convenience, is maintainable in both *Escherichia coli* and Streptomyces species, can be conjugally transferred from *Escherichia coli* to Streptomyces species and is capable of supporting synthesis of PHO when phaCAB$_{Re}$ operon from *Ralstonia eutropha* is cloned into it. The resultant genetically modified organism *Streptomyces lividans* TK64 utilizes alternate and cheap carbon source for efficient invention production of polyhydroxyoctanoate (PHO).

SUMMARY OF THE INVENTION

Accordingly, the main object of the present invention is to provide a process for the production of polyhydroxyoctanoate using a genetically modified *Streptomyces lividans* TK64.

Another object of the present invention is to construct a multifunctional *Escherichia coli*—Streptomyces species conjugative shuttle vector designated as pGTR760 capable of providing multiple cloning sites for cloning ease and convenience.

Still another objective of the present invention is to clone the *Ralstonia eutropha* phaCAB$_{Re}$ operon coding for polyhydroxyalkanoate synthesis gene, in the *Escherichia coli*—Streptomyces species multifunctional, conjugative shuttle vector designated as pGTR760, resulting thus in the creation of a new plasmid vector designated pCAB218 carrying all the genes required for polyhydroxyalkanoate production.

Yet another objective of the present invention is to introduce the plasmid pCAB218 into *Streptomyces lividans* TK64 to develop a genetically modified bacterium which produces polyhydroxyoctanoate (PHO) utilizing alternate and cheap carbon sources.

The present invention relates to a process for the production of polyhydroxyoctanoate by using recombinant *Streptomyces lividans* TK64 deposited at ATCC No. PTA1578. More particularly it relates to a method of construction of a multifunctional *Escherichia coli*—Streptomyces conjugative shuttle vector pGTR760 containing the polyhydroxyalkanoate biosynthesis operon phaCAB$_{Re}$ from *Ralstonia eutropha* and the development of a new vector designated as pCAB218, which is eventually used to develop recombinant *Streptomyces lividans* TK64, capable of producing polyhydroxyoctanoate (PHO) in substantial amounts when grown in a conventional mineral medium.

DETAILED DESCRIPTION OF THE INVENTION AND BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Accordingly the present invention provides a novel method for the production of polyhydroxyoctanoate using recombinant *Streptomyces lividans* TK64, said method comprising the steps of:

a) constructing a multifunctional *Escherichia coli*—Streptomyces sp. conjugative shuttle vector designated as pGTR760, b) cloning of the polyhydroxyalkanoate biosynthesis operon phaCAB$_{Re}$ from *Ralstonia eutropha* in pUC18 plasmid vector and recloning of the phaCAB$_{Re}$ operon from pUC18 into the pGTR760 vector resulting in the formation of a new conjugative shuttle vector designated as pCAB218, c) transforming *Escherichia coli* S17-1 with the plasmid pCAB218 to develop recombinant *Escherichia coli* S17-1, d) transforming *Escherichia coli* S17-1 with *Streptomyces lividans* TK64 to obtain genetically modified bacterium *Streptomyces lividans* TK64, and e) culturing the genetically modified *Streptomyces lividans* TK64 in a conventional medium and recovering polyhydroxyoctanoate (PHO).

The invention is illustrated by the accompanying drawings wherein.

Figure 1:
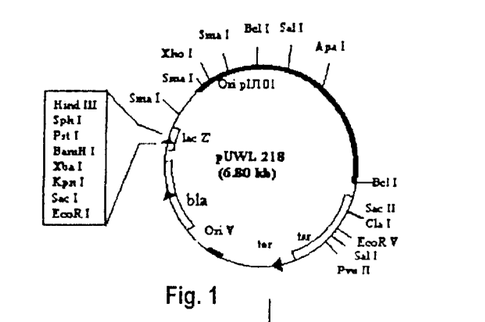
FIG. 1 represents the 6.8 kb pUWL218 plasmid: *Escherichia coli*—Streptomyces sp. shuttle vector which lacks conjugative capability. The Ori pIJ101: Sma I-Bcl I DNA fragment containing Streptomyces sp. replication origin; Ori V: *Escherichia coli* replication origin; lacZ: β galactosidase gene that allows blue/white selection in α-complementing *Escherichia coli* which also contains multiple cloning sites; bla: ampicillin resistance gene; tsr: thiostrepton resistance gene. Other relevant restriction sites are shown.
Figure 2:
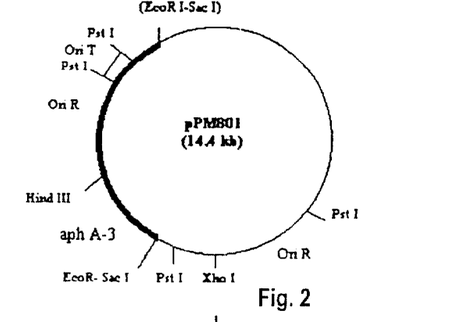
FIG. 2 represents the 14.4 kb pPM801 plasmid *Escherichia coli*—Streptomyces sp. conjugative vector containing the entire Sma I-Bcl I DNA fragment containing pIJ101 replicon which includes Streptomyces spread and transfer functions; OriR: *Escherichia coli* replication origin; OriT: 760 bp fragment containing origin of transfer of RK2 plasmid; EcoR I-Sac I: polylinker containing sites for EcoR I, Bgl II, Mlu I, BamH I, Sac I; term: bacteriophage fd transcriptional terminator; Ori R': Streptomyces sp. replication origin; aph A-3: neomycin resistance gene; the unique Hind III site available for cloning in pPM801. Other relevant restriction sites are shown.
Figure 3:
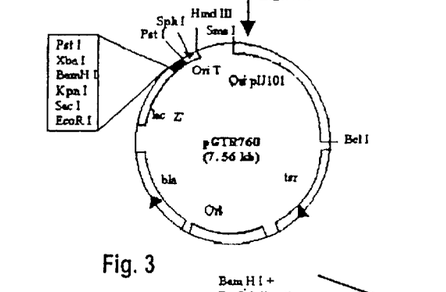
FIG. 3 represents the 7.56 kb pGTR760 plasmid: *Escherichia coli*—Streptomyces sp. conjugative shuttle vector containing multiple cloning sites which includes sites for restriction endonucleases PstI, Sal I(Hinc II), Xba I, BamHI, Kpn I, Sac I and EcoR I. The Ori pIJ101: Sma I-Bcl I DNA fragment containing Streptomyces sp. replication origin; Ori V: *Escherichia coli* replication origin; OriT: 760 bp fragment containing origin of transfer of RK2 plasmid; tsr: thiostrepton resistance gene; bla: ampicillin resistance gene.

The plasmid pPM801 is shown in FIG. 2 of the accompanying drawings. The shuttle vector pUWL218 is shown in FIG. 1 of the drawings and the new multifunctional conjugative shuttle vector pGTR760 is shown in FIG. 3.

In an embodiment, the 760 bp PstI restriction fragment containing the OriT origin of transfer of RK2 origin from the plasmid pPM801 was isolated and cloned into the PstI restriction site of the shuttle vector pUWL218 resulting in the development of a new multifunctional conjugative shuttle vector pGTR760.

Figure 4:
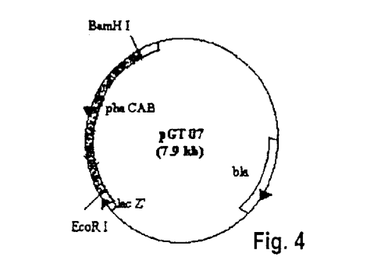
FIG. 4 represents the 7.9 kb pGT07 plasmid harbouring phaCAB$_{Re}$ operon from *Ralstonia eutropha* in pUC18. bla: ampicillin resistance gene.

In yet another embodiment, the EcoRI and SmaI restriction fragment from the genomic DNA of Ralstonia eutropha was shotgun cloned into cohesive and complementary EcoRI and SmaI restriction ends of the plasmid pUC18 to construct a subgenomic library. The library was screened with oligonucleotide probes homologous to the 5'-region of the phaC gene, the 5'-region of the phaA gene and the 3'-region of the phaB gene from Ralstonia eutropha, and a clone which gave positive signal to all the three oligonucleotide probes was isolated, characterized and designated as pGT07 as shown in FIG. 4 of the drawings.

Figure 5:
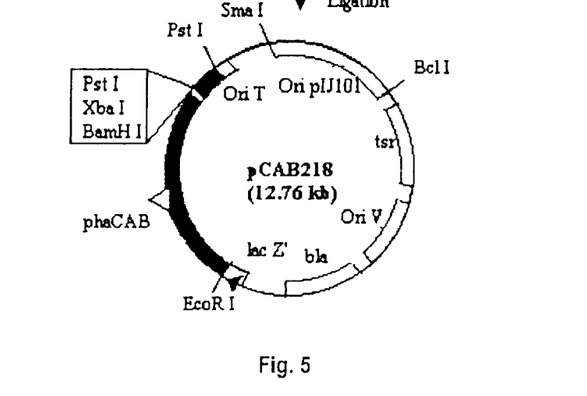
FIG. 5 represents the 12.76 kb pCAB218 plasmid: pGTR760 plasmid containing phaCAB$_{Re}$ operon from *Ral-* stonia eutropha. The Ori pIJ101: Streptomyces sp. replication origin; Ori V:Escherichia coli replication origin; OriT: 760 bp fragment containing origin of transfer of RK2 plasmid; tsr: thiostrepton resistance gene; bla: ampicillin resistance gene; multiple cloning sites which include sites for restriction endonucleases PstI, Xba I, BamH I.

In yet another embodiment, the pGT07 plasmid vector was restriction digested with EcoRI and BamHI, the approximate 5 kb EcoRI-BamHI DNA fragment carrying the phaCAB$_{Re}$ polyhydroxyalkanoates biosynthesis operon from Ralstonia eutropha was isolated, purified and then cloned into the compatible EcoRI and BamHI restriction sites of the multifunctional conjugative shuttle vector pGTR760. This resulted in the preparation of the new recombinant, multifunctional conjugative shuttle vector pCAB218 as shown in FIG. 5 of the drawings which also carried all the genes required for the production of polyhydroxyalkanoates.

In still another embodiment, Escherichia coli S17-1 was then transformed with the plasmid pCAB218 by standard methods.

In another embodiment, the recombinant Escherichia coli S17-1 was mated with Streptomyces lividans TK64 using standard methods to transform and develop recombinant Streptomyces lividans TK64. The genetically modified Streptomyces lividans TK64 has been deposited in National Collection of Industrial Microorganisms (NCIM), Pune, India under accession number 5129. The strain has also been deposited at the American Type Culture Collection, 10801, University Boulevard, Manassas, Va. 20110, U.S.A. on Apr. 25, 2000 under accession number ATCC PTA 1578. This genetically modified strain Streptomyces lividans TK64 harboring the conjugative shuttle plasmid vector pCAB218 expresses gene for thiostrepton resistance and polyhydroxyoctanoate biosynthetic operon from Ralstonia eutropha. The original Streptomyces lividans TK64 strain was procured from ATCC and bears accession number 19844. The genetically modified organism Streptomyces lividans TK64 (ATCC No. PTA-1578) harboring pCAB218 conjugative shuttle plasmid vector utilizes glycerol as a carbon source for the synthesis of polyhydroxyoctanoate. However, with the use of other carbon sources individually or in combination it may be possible to order the synthesis of the other homo- or co-polymers of hydroxyalkanoates.

In yet another embodiment, recombinant Streptomyces lividans TK64 harboring pCAB218 plasmid vector when grown in a conventional mineral medium containing an alternate and cheap carbon source produces polyhydroxyoctanoate (PHO).

The plasmid pPM801 as shown in FIG. 2 of the drawings was digested with restriction endonuclease PstI to release 760 bp OriT DNA fragment. The pUWL218 plasmid vector as shown in FIG. 1 of the drawings was digested with PstI and the 760 bp OriT DNA fragment was ligated to it at 14–16° C. in presence of T4 DNA ligase enzyme for a period ranging between 16 to 18 hours to obtain new conjugative shuttle vector pGTR760 as shown in FIG. 3 of the drawings. The multifunctional Escherichia coli—Streptomyces species conjugative shuttle vector pGTR760 contains the replication function of the Streptomyces wide host range multicopy plasmid pIJ101, the tsr gene conferring resistance to thiostrepton in Streptomyces, the ColE I origin of replication from pBR322 for replication in Escherichia coli, the transfer function OriT of RK2 origin and the bla gene conferring ampicillin resistance in Escherichia coli. It also possesses unique multiple cloning sites for restriction endonucleases PstI, Xba I, BamHI, KpnI, SacI and EcoRI. Escherichia coli S17-1 when transformed with pGTR760 vector does not produce or accumulate any polyhydroxyalkanoates (PHAs). The synthesis and extent of polyhydroxyoctanoate (PHO) production in Streptomyces lividans TK64 also does not change when transformed with vector pGTR760.

The Ralstonia eutropha genomic DNA was restriction digested with EcoR I and Sma I. This restriction digested genomic DNA was shotgun cloned and ligated at 14–16° C. for 16–18 hours in presence of T4 DNA ligase enzyme to compatible and cohesive restriction end EcoRI and SmaI of the pUC18 plasmid. The ligated DNA was then used to transform Escherichia coli DH5α using standard methods. The recombinant E. coli colonies were then sequentially screened by standard colony hybridization procedure with oligonucleotide probes 5'-(d)GGACTACACAATGACTGACG-3' homologous to the 5'-region of the phaC gene, 5'-(d)ATCAAATCATGGCGACCGGC-3' homologous to the 5'-region of the phaA gene and 5'-(d)GGACGAAGATGGTGCTGGC-3' homologous to the 3'-region of the phaB gene of Ralstonia eutropha. Hybridization was carried out at 42° C. for 16 hours followed by washes at the same temperature. Clones that gave positive hybridization signals to all the three oligonucleotide probes were isolated and plasmid DNA was isolated from these. The plasmid DNA upon restriction digestion with EcoRI and Sma I released an approximate 5.0 kb insert and was designated pGT07 as shown in FIG. 4 of the drawings. The pGT07 plasmid was next restriction digested with EcoRI and BamHI to release the phaCAB$_{Re}$ operon insert, which was isolated and purified by agarose gel electrophoresis. The conjugative shuttle vector pGTR760 containing the multiple cloning sites was restriction digested with EcoRI and BamHI and the phaCAB$_{Re}$ operon which already contained compatible EcoRI and BamHI ends, was ligated to it. This resulted in the preparation of the multifunctional conjugative shuttle vector pCAB218 as shown in FIG. 5 of the drawings which also carried all the genes necessary for the synthesis and accumulation of polyhydroxyalkanoate. The ligated product was then transformed into *Escherichia coli* S17-1. Individual recombinant *Escherichia coli* S17-1 colonies were picked and separately inoculated into ampicillin (50–200 µg/ml) containing Luria Bertani broth [Sambrook J., Fritch, E. F. and Maniatis, T., *Molecular cloning: A Laboratory manual*, $2^{nd}$ ed., Cold Spring Harbor Laboratory Press, Cold Spring Harbor, N.Y. 1989]. The recombinant *Escherichia coli* S17-1 harboring the plasmid pCAB218 was mated with *Streptomyces lividans* TK64. This facilitated conjugal transfer of the plasmid pCAB218 from recombinant *Escherichia coli* S17-1 to *Streptomyces lividans* TK64. About 1 to $3\times10^3$ transformants per plate were recovered. The recombinant *Streptomyces lividans* TK64 were selected on thiostrepton (50–200 µg/ml) and nalidixic acid (150–400 µg/ml) containing Luria Bertani broth medium. The natural resistance of *Streptomyces lividans* TK64 was exploited to counter select the sensitive donor *Escherichia coli* S17-1 and thiostrepton resistance was used to select for transconjugant, recombinant *Streptomyces lividans* TK64 harboring the pCAB218 plasmid. The individual recombinant *Streptomyces lividans* TK64 colonies were inoculated into MGYP broth medium [Hopwood, D. A., Bibb, M. I., Chater, K. F., Kieser, T., Bruton, C. J., Kieser, H. M., Lydiate, D. J., Smith, C. P., Ward, J. M. and Scrempf, H., *Genetic Manipulation Of Streptomyces; A Laboratory Manual*. John Innes Foundation, Norwich, England, 1985]. The transformants showed normal sporulation and growth rates on medium slants and in rich as well as minimal medium supplemented with 10–100 µg/ml thiostrepton. The plasmid pCAB218 was stably maintained in the transformant. The recombinant *Streptomyces lividans* TK64 deposited with NCIM, Pune (NCIM 5129) and ATCC, U.S.A (ATCC PTA 1578) was grown in a conventional mineral medium containing glycerol (0.5 to 5.0%) as the alternative carbon source was found to produce polyhydroxyoctanoate (PHO).

The present invention provides the pCAB218 multifunctional conjugative shuttle plasmid vector which also contains the polyhydroxyalkanoate biosynthesis phaCAB$_{Re}$ operon, which when introduced into *Streptomyces lividans* TK64 makes the recombinant bacterium produce polyhydroxyoctanoate in substantial amounts. The recombinant *Streptomyces lividans* TK64 is grown in a conventional mineral medium containing (g/L): glycerol 5–50; L-asparagine 0.5–1.5; $K_2HPO_4$ (anhydrous) 0.5–1.5; trace salt solution 0.5–1.5 ml; distilled water pH7.0. The trace salt solution contained (100 ml): $FeSO_4.7H_2O$ 50–150 mg; $MnCl_2.4H_2O$ 50–150 mg; $ZnSO_4.7H_2O$ 50–150 mg and distilled water, for 80 to 120 hours at a temperature ranging between 25 to 35° C. The biomass is seperated after harvesting the medium and treated by conventional methods like solvent extraction using sodium hypochlorite and chloroform.

Figure 6A:
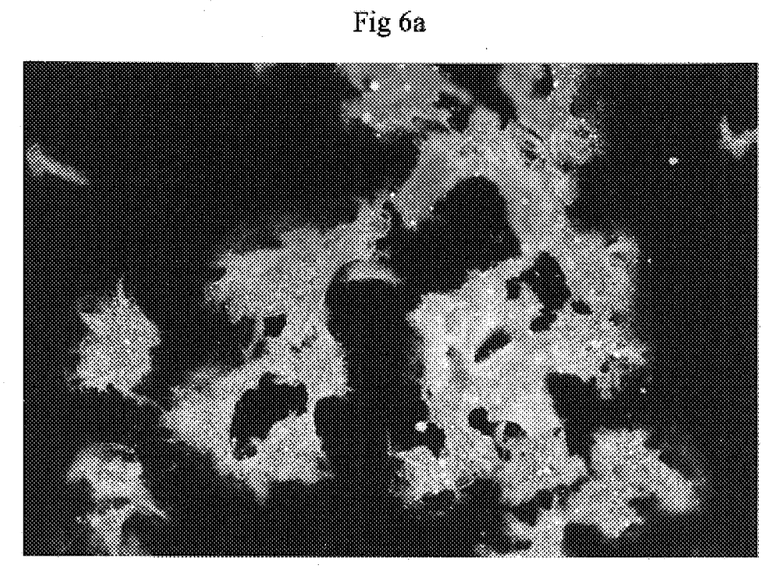
FIG. 6a and 6b represent respective fluorescence photomicrographs of the non-recombinant and the recombinant Streptomyces lividans TK64, the latter deposited as NCIM 5129 and being on deposit at the ATCC under accession number ATCC PTA-1578, stained with Nile blue A.
Figure 6B:
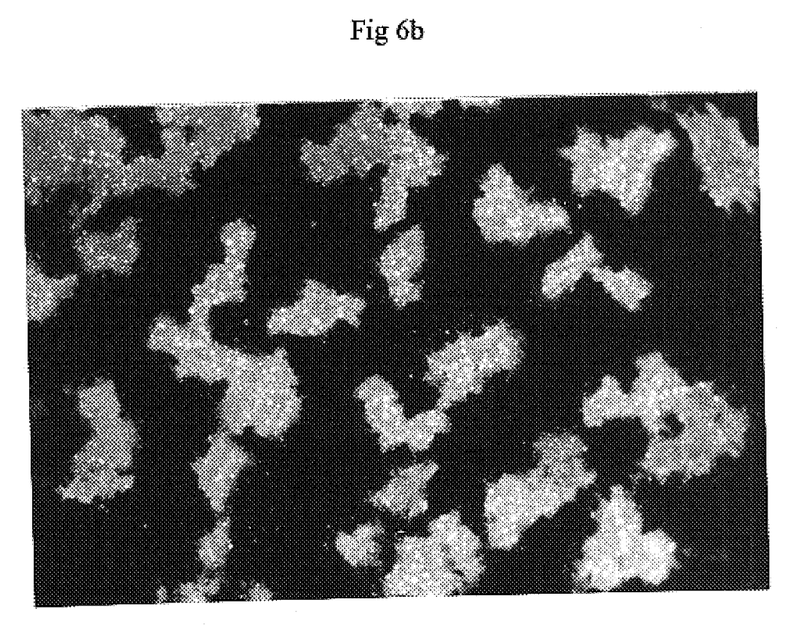

The polyhydroxyoctanoate production was observed in both, the nontransformed and the transformed *Streptomyces lividans* TK64 by fluorescence microscopy when stained by Nile blue A (FIGS. 6a and 6b).

Figure 7A:
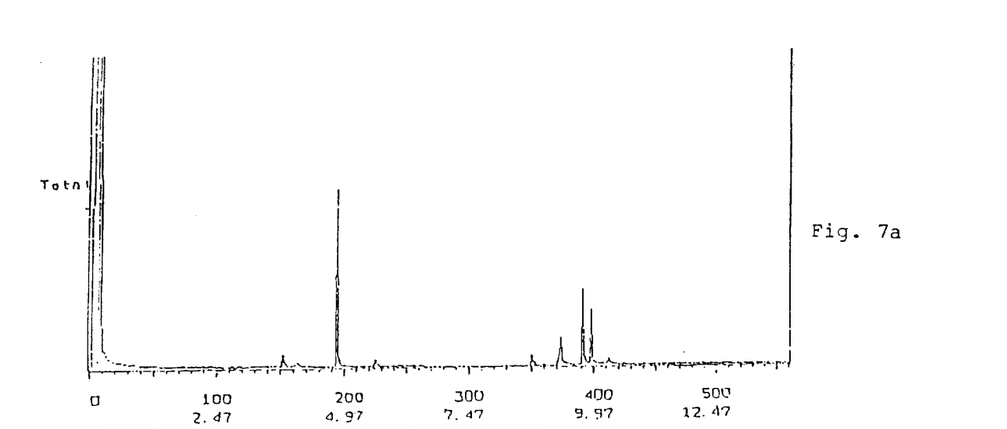
FIG. 7a, 7b and 7c represent respectively gas chromatogram and GC-MS of propyl ester of polyhydoxyoctanoate from recombinant Streptomyces lividans TK64 bearing accession number NCIM 5129 (ATCC PTA-1578).
Figure 7B:
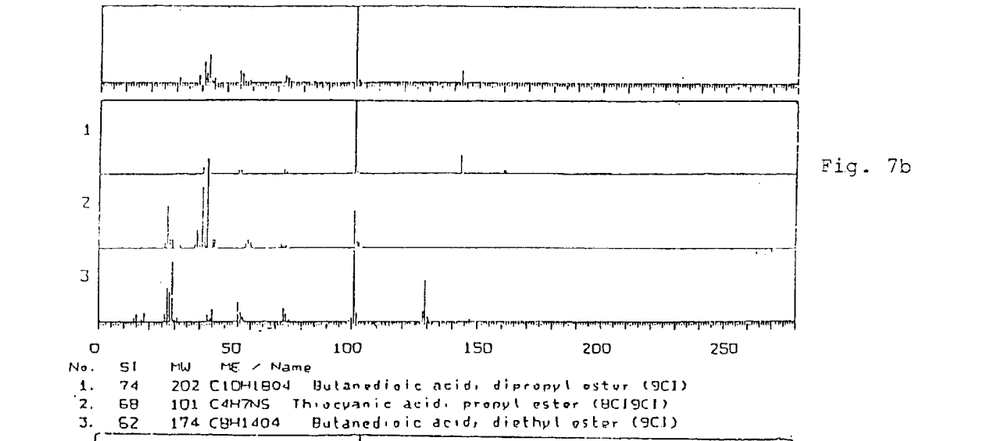
Figure 7C:
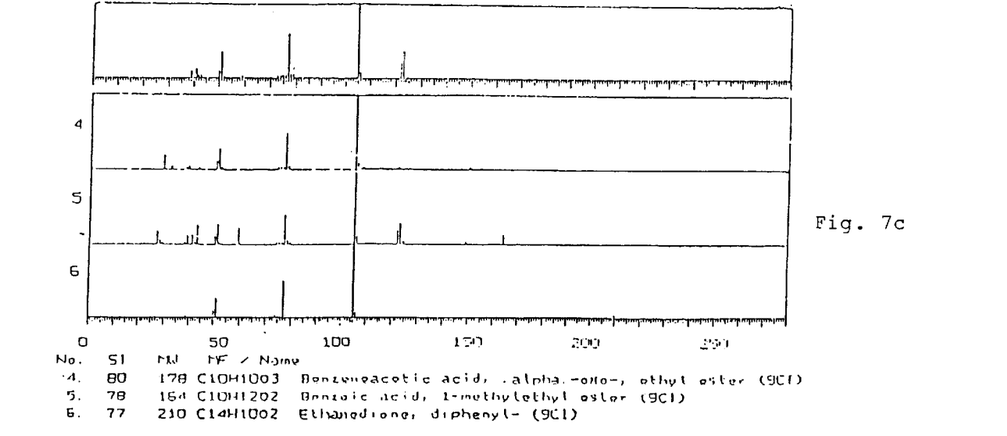

As shown in FIGS. 7a, 7b and 7c of the drawings, gas-chromatography [Riis, V. and Mai, W., J. Chromatogr., 445 (1988) 285–289] and GC-MS analysis revealed that the transformed *Streptomyces lividans* TK64 produced and accumulated polyhydroxyoctanoate (PHO) instead of the more common poly-β-hydroxybutyrate (PHB).

The method for the preparation of the vector and the recombinant *Streptomyces lividans* TK64 of the present invention is described herein below. An aspect of the process resides in the production of polyhydroxyoctanoate by genetically modified *Streptomyces lividans* TK64 harboring pCAB218 vector which is but a pGTR760 vector into which the polyhyroxyalkanoate operon from *Ralstonia eutropha* has been cloned. The merit of the process is that polyhydroxyoctanoate is ordered by the genes from a DNA fragment which directs polyhydroxybutyrate synthesis in *Ralstonia eutropha*. The product polyhydroxyoctanoate is synthesized by the genetically modified *Streptomyces lividans* TK64 using glycerol as a carbon source. The novelty of the process also resides in the construction and usage of a new vector pGTR760 which can be transferred from *Escherichia coli* to Streptomyces sp. both by conjugal or physical means and allows the expression of cloned genes in both the organisms. The above said vector as against other conventionally available vectors provides multiple cloning sites for directional cloning allowing the user to choose restriction site(s) of choice for cloning.

EXAMPLES

The following examples are given by way of illustration and therefore should not be construed to limit the scope of the present invention.

Example 1

Formation of Linearized Plasmid pUWL218

Plasmid pUWL218 was incubated at 37° C. with restriction endonuclease PstI in 1× reaction buffer L (Amersham-USB) for 3 hours. The linearized plasmid pUWL218 was obtained.

Example 2

Isolation of Fragment Carrying OriT

Plasmid pPM801 was incubated at 37° C. with restriction endonuclease PstI in 1× reaction buffer L (Amersham-USB) for 3 hours. The digested DNA sample was separated by electrophoresis on 1% agarose gel and the 760 bp fragment carrying the OriT origin of transfer from RK2 plasmid was isolated and purified.

Example 3

Formation of Shuttle Vector pGTR760

The linearized pUWL218 and the 760 bp OriT origin of transfer (example 2) were ligated at 14–16° C. with the help of T4 DNA ligase for 16 to 18 hours. The ligation product resulted in the preparation of *Escherichia coli*—Streptomyces conjugative shuttle vector pGTR760.

Example 4

Formation of Recombinant Plasmid Vector pCAB218

The pGTR760 plasmid was incubated with restriction endonucleases EcoR I and BamH I in 1× reaction buffer K (Amersham-USB) at 37° C. for 3 hours.

An approximate 5 kb DNA fragment containing the phaCAB$_{Re}$ operon was isolated. This was done by screening an EcoR I-Sma I subgenomic library of *Ralstonia eutropha* with oligonucleotide probes homologous to phaC, phaA and phaB genes. The approximate 5.0 kb fragment contained cohesive ends compatible for cloning in Sma I and EcoR I sites. This fragment was ligated to Sma I/EcoR I digested pUC18 vector. The resulting plasmid is designated as pGT07 as shown in FIG. 4 of the drawings. For Sma I digestion, DNA sample was incubated at 30° C. in 1× buffer T and Sma I enzyme (Amersham-USB) for 3 hours. For EcoR I digestion, DNA sample was incubated at 37° C. in 1× buffer H and EcoR I enzyme(Amersham-USB) for 3 hours.

The pGT07 plasmid was incubated with restriction endonucleases EcoR I and BamH I in 1× reaction buffer K (Amersham-USB) at 37° C. for 3 hours to release the phaCAB$_{Re}$ operon from the vector.

The restriction digested plasmid vector pGTR760 and the phaCAB$_{Re}$ operon (example 6) were ligated at 14–16° C. with the help of T4 DNA ligase for 16 to 18 hours. The ligation product lead to the creation of the recombinant plasmid vector pCAB218 which carried all the genes responsible for the synthesis of polyhydroxyalkanoates. The protocol for ligation was as advised by the manufacturer of the enzyme.

Example 5

Transformation of *E.Coli* S17-1 with Recombinant Vector

*Escherichia coli* S17-1 was then transformed with the ligation product, i.e. recombinant plasmid vector pCAB218. Preparation of competent *Escherichia coli* S17-1 cells and their transformation was done using standard methods [Sambrook, J., Fritsch, E. F. and Maniatis, T., Molecular Cloning: A Laboratory manual, 2nd ed., Cold Spring Harbor Laboratory Press, Cold Spring Harbor, N.Y. 1989]. The selection was on Luria Bertani agar medium (1.0% bactotryptone, 0.5% yeast extract, 1.0% Sodium chloride; pH 7.0) plates containing 50–200 μg/ml ampicillin. The recombinant plasmid pCAB218 was isolated from the above selected colonies in large quantities by alkaline lysis method [Sambrook, J., Fritsch, E. F. and Maniatis, T., Molecular Cloning: A Laboratory manual, 2nd ed., Cold Spring Harbor Laboratory Press, Cold Spring Harbor, N.Y., 1989].

The recombinant *Escherichia coli* S17-1 were grown overnight at 37° C. in 50 ml LB medium broth supplemented with 50–200 μg/ml ampicillin. Cells were then pelleted by centrifugation at 4000×g for 5 minutes at 4° C. and resuspended in 1–10 ml LB medium broth (1.0% bactotryptone, 0.5% yeast extract, 1.0% sodium chloride, pH 7.0).

Example 6

Mating of *E.coli* S17-1 with *Streptomyces lividans* TK64

The *Streptomyces lividans* TK64 spores were induced to germinate by heat shock at 42° C., pelleted by centrifugation at 4000×g for 5 minutes at 4° C. and resuspended in 1–10 ml LB medium broth.

The donor (0.1–1.0 ml recombinant *Escherichia coli* S17-1) and the recipient (0.1–1.0 ml *Streptomyces lividans* TK64 germinated spores) were mixed in 10:1 to 1:10 ratio and spread on LB medium agar plates. The cells were allowed to mate overnight at 28° C. on LB agar plates. The LB agar plates were washed repeatedly with fresh LB medium broth to remove *Escherichia coli* S17-1 cells. The plates were allowed to dry and overlaid with 1–5 ml LB medium broth containing 50–300 μg thiostrepton and 150–400 μg nalidixic acid to select transconjugants.

Six days later about 1 to 3×10³ transconjugant *Streptomyces lividans* TK64 per plate were recovered. Individual colonies were isolated and grown at 25–35° C. for 4 days for sporulation on MGYP medium agar slants (malt extract 0.1–2.0%; glucose 0.4–4.0%; yeast extract 0.1–3.0% and peptone 0.2–5.0%; pH 7.0) supplemented with thiostrepton (10–100 g/ml).

Example 7

Culturing of Recombinant *Streptomyces Lividans* TK64 & Production of Polyhydroxyoctanoate (PHO)

MGYP medium broth (50 ml) supplemented with thiostrepton (10–100 g/ml) was inoculated with spores from recombinant *Streptomyces lividans* TK64 grown on slants and allowed to grow to an absorbance of 1.0–6.0 at 640 nm with constant shaking at 25–35° C.

Recombinant *Streptomyces lividans* TK64 cells (example 16) were pelleted down by centrifugation at 4000×g for 5 minutes at 4° C. washed with saline and repelleted.

The pelleted recombinant *Streptomyces lividans* TK64 cells were re-suspended to make a 0.5–5.0% inoculum in mineral medium containing (g/L): glycerol 5–50; L-asparagine 0.5–1.5; K2HPO4 (anhydrous) 0.5–1.5; trace salt solution 0.5–1.5 ml; distilled water pH7.0. The trace salt solution contained (100 ml): FeSO4.7H2O 50–150 mg; MnCl2.4H2O 50–150 mg; ZnSO4.7H2O 50–150 mg and distilled water to makeup volume. The cells were allowed to grow at 25–35° C. Non-transformed, wild type *Streptomyces lividans* TK64 was also grown from a 0.5–5.0% inoculum on mineral medium. The genetically engineered *Streptomyces lividans* TK64 produced at least 7.5% polyhydroxyoctanoate (PHO) in 80 to 120 hours when allowed to grow in culture. The non-recombinant *Streptomyces lividans* TK64 produced a maximum of 1.75% polyhydroxyoctanoate (PHO) in 80 to 120 hours when allowed to grow in culture.

Some ADVANTAGES of the present invention are:

1. The newly created vector pGTR760 is an *Escherichia coli*—Streptomyces conjugative shuttle vector which provides multiple cloning sites for cloning ease and convenience.

2. The newly created vector pCAB218 is an *Escherichia coli*—Streptomyces conjugative shuttle vector which also has a nucleic acid sequence cloned in it which codes for PHA biosynthesis genes.

3. *Streptomyces lividans* TK64 when transformed with pCAB218 produces polyhydroxyoctanoate (PHO) utilizing glycerol as the alternate carbon source.

What is claimed is:

1. A multifunctional *Escherichia coli*—Streptomyces sp. conjugative shuttle vector designated as pGTR760 (SEQ ID No.:1) containing multiple cloning sites, the vector being formed by a process comprising ligating a 760 bp Ori T PstI restriction fragment from plasmid pPM801 with plasmid pUWL218 at a temperature in the range of 14–16° C. in the presence of T4 DNA ligase enzyme for a period ranging between 16 to 18 hours.

2. A recombinant *Escherichia coli*—Streptomyces conjugative shuttle vector pCAB218 (SEQ ID No.:2) cloned with a nucleic acid sequence coding for genes responsible for polyhydroxyalkanoate synthesis, the vector being formed by a process comprising cloning the polyhydroxyalkanoate synthesis operon phaCAB$_{Re}$ obtained from *Ralstonia eutropha* into the EcoRI-BamHI restriction sites of the vector pGTR760 of claim 1.

3. An isolated/purified culture of recombinant *Streptomyces lividans* TK64 bacterium bearing ATCC No. PTA 1578, said bacterium harbouring pCAB218 plasmid and capable of producing polyhydroxyoctanoate (PHO) in substantial amounts.

4. A process for the production of polyhydroxyoctanoate, comprising:
   a) constructing a multifunctional *Escherichia coli*—Streptomyces sp. conjugative shuttle vector designated as pGTR760, (SEQ ID No.:1) the vector being formed by a process comprising ligating a 760 bp Ori T PstI restriction fragment from plasmid pPM801 with plasmid pUWL218 at a temperature in the range of 14–16° C. in the presence of T4 DNA ligase enzyme for a period ranging between 16 to 18 hours;
   b) cloning of the polyhydroxyalkanoate biosynthesis operon phaCAB$_{Re}$ from *Raistonia eutropha* in pUC18 plasmid vector and recloning of the phaCAB$_{Re}$ operon from pUC18 into the pGTR760 vector resulting in the formation of a new conjugative shuttle vector designated as pCAB218, (SEQ ID No.:2)
   c) transforming *Escherichia coli* S17-1 with the plasmid pCAB218 to develop recombinant *Eseherichia coli* S17-1,
   d) transforming *Escherichia coli* S17-1 with *Streptomyces lividans* TK64 to obtain genetically modified bacterium *Streptomyces lividans* TK64, and
   e) culturing the genetically modified *Streptomyces lividans* TK64 in a medium and recovering polyhydroxyoctanoate (PHO).

5. A process as claimed in claim 1 wherein the multifunctional *Escherichia coli*-Streptomyces species conjugative shuttle vector pCAB218 is developed by cloning the polyhydroxyalkanoate synthesis operon phaCAB$_{Re}$ obtained from *Ralstonia eutropha* into the EcoRI-BamHI restriction sites of the vector pGTR760.

6. A process as claimed in claim 1 wherein the medium comprises glycerol, asparagine and salts.

7. A process as claimed in claim 1 wherein the medium comprises glycerol, L-aspargine, distilled water and salts selected from anhydrous $K_2HPO_4$, $FeSO_4.7H_2O$, $MnCl_2.4H_2O$ and $ZrSO_4.7H_2O$.

* * * * *